United States Patent
Yuan et al.

(10) Patent No.: US 6,977,141 B2
(45) Date of Patent: Dec. 20, 2005

(54) DIRECT ADSORPTION SCINTILLATION ASSAY FOR MEASURING ENZYME ACTIVITY AND ASSAYING BIOCHEMICAL PROCESSES

(75) Inventors: Zhengyu Yuan, Fremont, CA (US); Zhong-Xiao Chen, Belmont, CA (US)

(73) Assignee: Vicuron Pharmaceuticals Inc., Fremont, CA (US)

( * ) Notice: Subject to any disclaimer, the term of this patent is extended or adjusted under 35 U.S.C. 154(b) by 257 days.

(21) Appl. No.: 09/248,158

(22) Filed: Feb. 9, 1999

(65) Prior Publication Data

US 2002/0015678 A1 Feb. 7, 2002

Related U.S. Application Data

(60) Provisional application No. 60/074,272, filed on Feb. 10, 1998.

(51) Int. Cl.$^7$ .............................. C12Q 1/00; C12Q 1/44
(52) U.S. Cl. .............................. 435/4; 435/7.1; 435/7.2; 436/57; 436/501; 436/518; 436/542; 424/1.11
(58) Field of Search .............................. 435/4, 7.1, 7.2; 436/57, 501, 518, 542, 537; 424/1.11; 422/102; 250/370.11

(56) References Cited

U.S. PATENT DOCUMENTS

| | | | |
|---|---|---|---|
| 4,271,139 A | 6/1981 | Hart .............................. | 424/1 |
| 4,382,074 A | 5/1983 | Hart .............................. | 436/537 |
| 4,388,296 A | 6/1983 | Hart .............................. | 424/1 |
| 4,451,434 A | 5/1984 | Hart .............................. | 422/102 |
| 4,568,649 A | 2/1986 | Bertoglio-Matte .............. | 436/534 |
| 4,868,300 A | 9/1989 | Kuhla et al. .................. | 544/119 |
| 5,415,995 A | 5/1995 | Schoolnik et al. ............ | 435/7.1 |
| 5,466,930 A | 11/1995 | Schlemoff .................... | 250/252.1 |
| 5,605,616 A | 2/1997 | Zepp ............................ | 205/688 |
| 5,665,562 A | 9/1997 | Cook ........................... | 435/35 |
| 5,891,621 A | 4/1999 | Chabin et al. | |
| 5,972,595 A | * 10/1999 | Kasila et al. ................. | 435/4 |

FOREIGN PATENT DOCUMENTS

| | | |
|---|---|---|
| EP | 0 154 734 B1 | 9/1985 |
| EP | 0 378 059 B1 | 7/1990 |
| EP | 0 438 470 B1 | 7/1991 |
| WO | WO 88/04429 | 6/1988 |
| WO | WO 90/03844 | 4/1990 |
| WO | WO 96/15258 | 5/1996 |

OTHER PUBLICATIONS

Brown et al. FlashPlate Technology. 1997. High Throughput Screening, Editor: Devlin, J. P. NY, NY. pp. 317–328.*
Baker et al., "A scintillation proximity assay for UDP-GalNAc: Polypeptide, N–acetylgalactosaminyltransferase" *Analytical Biochemistry* 239:20–24 (1996).

Baxendale et al., "Development of scintillation proximity assays for prostaglandins and related compounds" *Advances in Prostaglandin, Thromboxane, and Leukotriene Research* Sameulsson et al., ed., Raven Press, Ltd., New York, 21:303–306 (1990).
Cook, Neil D., "Scintillation proximity assay: a versatile high–throughput screening technology" *Drug Discovery Today* 1:287–294 (1996).
Hart et al., "Scintillation–proximity assay of particulate binding properties" *Biophysical Journal*, Mar. 1978, vol. 21, No. 3, (Abstract).
Hart et al., "Scintillation proximity assay (SPA) of antigen–antibody binding kinetics" The *Journal of Nuclear Medicine*, Jun. 1978, vol. 19, No. 6, (Abstract).
Hart et al., "Scintillation proximity assay (SPA)—a new method of immunoassay" *Molecular Immunology* 16:265–267 (1979).
Hawkins, Edward F., "Solid scintillators for receptor assays: An environmentally safe alternative to liquid scintillating cocktails" *Journal of Receptor Research* 11:91–99 (1991).
Ihalainen et al., "Towards automatic detection of point mutations: Use of scintillating microplates in solid–phase minisequencing" *BioTechniques* 16:938–943 (1994).
Matsumura et al., "A simple method for measurement of phosphoramidon–sensitive endothelin converting enzyme activity" *Life Sciences* 51:1603–1611 (1992).
Nelson, Nathan, "A novel method for the detection of receptors and membrane proteins by scintillation proximity radioassay" *Analytical Biochemistry* 165:287–293 (1987).
Rabe et al., "New assays for the enzymatic conversion of cholesterol to pregnenolone" *Steroids* 37:555–571 (1981).
Swinkels et al., "Scintillation proximity assay: determination of steroid hormones without separation of antibody–bound and free ligand" *Ann Clin Biochem* 28:87–90 (1991).
Udenfriend et al., "Scintillation proximity assay: A sensitive and continuous isotopic method for monitoring ligand/receptor and antigen/antibody interactions" *Analytical Biochemistry* 161:494–500 (1987).

* cited by examiner

*Primary Examiner*—Bennett Celsa
(74) *Attorney, Agent, or Firm*—Thomas R. Savitsky

(57) ABSTRACT

Methods and materials for scintillation assays are disclosed. The scintillation assays rely on differences in general molecular property-based binding interactions, such as charge or hydrophobicity, to localize a radioactive substance near a scintillating material, stimulating scintillation. They are thus described as a direct adsorption scintillation assay (DASA) to distinguish them from the scintillation proximity assay (SPA). The assays are more convenient and inexpensive to implement than SPAs, which rely on specific binding of ligand-receptor pairs, antibody-antigen pairs, or other binding partners which rely on the precise and specific structural complementarity of the partners. The assays can be employed for studying enzymatic reactions, such as those involved in the synthesis of Mur-pentapeptide. The assays are readily adaptable to high throughput screening for use in conjunction with combinatorial libraries of compounds.

17 Claims, 5 Drawing Sheets

MurC Assay in Two Plates (MurC_NEN/VDCD)

SEQUENCE LISTING

<160> NUMBER OF SEQ ID NOS: 4

<210> SEQ ID NO 1
<211> LENGTH: 7
<212> TYPE: PRT
<213> ORGANISM: Unknown
<220> FEATURE:
<223> OTHER INFORMATION: Synthetic peptide
<221> NAME/KEY: MOD_RES
<222> LOCATION: (2)...(2)
<223> OTHER INFORMATION: 3H attached to Leucine

<400> SEQUENCE: 1

Pro Leu Gly Leu Leu Ala Arg
 1               5

<210> SEQ ID NO 2

-continued

```
<211> LENGTH: 4
<212> TYPE: PRT
<213> ORGANISM: Unknown
<220> FEATURE:
<223> OTHER INFORMATION: Synthetic peptide

<400> SEQUENCE: 2

Leu Leu Ala Arg
 1

<210> SEQ ID NO 3
<211> LENGTH: 12
<212> TYPE: PRT
<213> ORGANISM: Unknown
<220> FEATURE:
<223> OTHER INFORMATION: Synthetic peptide

<400> SEQUENCE: 3

Pro Leu Ser Arg Thr Leu Ser Val Ala Ala Lys Lys
 1               5                  10

<210> SEQ ID NO 4
<211> LENGTH: 19
<212> TYPE: PRT
<213> ORGANISM: Unknown
<220> FEATURE:
<223> OTHER INFORMATION: Synthetic peptide
<221> NAME/KEY: MOD_RES
<222> LOCATION: (15)...(15)
<223> OTHER INFORMATION: 32P-phosphate attached to Serine

<400> SEQUENCE: 4

Asp Leu Asp Val Pro Ile Pro Gly Arg Phe Asp Arg Arg Val Ser Val
 1               5                  10                  15

Ala Ala Glu
```

DIRECT ADSORPTION SCINTILLATION ASSAY FOR MEASURING ENZYME ACTIVITY AND ASSAYING BIOCHEMICAL PROCESSES

CROSS-REFERENCE TO RELATED APPLICATIONS

This application claims priority benefit of co-pending U.S. Provisional Patent Application Ser. No. 60/074,272 filed Feb. 10, 1998. The content of that application is hereby incorporated herein in its entirety.

STATEMENT OF RIGHTS TO INVENTIONS MADE UNDER FEDERALLY SPONSORED RESEARCH

Not applicable.

TECHNICAL FIELD

This invention relates to methods for analyzing samples, particularly biological and biochemical samples such as reaction substrates or products, using scintillation assays. The scintillation assays utilize differences in the molecular properties between reactants and products, such as net charge or hydrophobicity, to enable selected radiolabeled substrates or products to bind to the scintillant. These assays are convenient and inexpensive.

BACKGROUND ART

Scintillation assays are commonly used for a variety of analytical purposes. The phenomenon of scintillation arises when a radioactive particle, such as a negative β-particle (an electron) interacts with and excites (raises above its ground state) certain substances. The excited substance emits light as it returns to its ground state. This process is referred to as scintillation; a substance capable of emitting light via the scintillation process is referred to as a scintillant. The flashes of light can be counted easily by a variety of devices. Assays which rely on scintillation have become widespread because of the ease and accuracy with which the radioactivity can be quantitated.

Electrons emitted by individual radioactive negative β-emitting substances are emitted at one or more distinct energies. Because of the distinct energies, electrons emitted by a specific radioactive material have a distinct pathlength in an aqueous environment. (If a material emits electrons at more than one distinct energy, there will be a corresponding pathlength for each energy.) For example, $^3$H (tritium) emits an electron with a pathlength of approximately 1.5 μm in aqueous solution. (Approximately 90% of the electrons emitted by tritium are absorbed within 1 μm in water, and the maximum range is approximately 8 μm.) $^{125}$I emits two electrons with pathlengths of approximately 1 μm and 17.5 μm, respectively. Cook, Drug Discovery Today 1:287 (1996); and Udenfriend et al., Analytical Biochemistry 161:494 (1987).

Scintillation proximity assay (SPA) makes use of the limited pathlength of certain electron-emitters. Hart et al., Molecular Immunology 16:265 (1979); Hart, U.S. Pat. Nos. 4,271,139 and 4,382,074; and Bertoglio-Matte, U.S. Pat. No. 4,568,649. An exemplary SPA is composed of an analyte in solution, plastic beads which scintillate when exposed to electrons, and a specific binding partner (such as an antibody) bound to the beads and specific for the analyte in solution. If the analyte incorporates a radioactive label which emits electrons of relatively short pathlength, such as tritium, the plastic beads will only scintillate when suspended in solution with the radioactive analyte when the analyte is specifically bound by the binding partner and thus localized near the surface of the beads.

One typical application of such an assay is measuring completion of an enzyme-catalyzed reaction. An antibody specific for the product of the reaction and which does not cross-react with the substrate of the reaction is attached to the scintillating material. The substrate is labeled with tritium, and the reaction allowed to proceed. The antibody-coated beads are added to the reaction mixture at a certain time point. The radioactive product will be localized to the surface of the beads, causing scintillation. Substrate molecules, although radioactive, remain unbound and are, on average, too far away from the beads to produce significant scintillation due to the short pathlength of the electron emitted by tritium. Care must be taken to ensure that such background scintillation is kept to an acceptably low level; for example, an extremely high concentration of substrate may lead to unacceptably high background scintillation. Low background levels are accounted for by suitable controls.

SPAs have been developed and exploited for a variety of analytical purposes. SPAs have been used for radioimmunoassays, competition assays, enzyme kinetic assays, studies of ligand/receptor and antigen/antibody interactions, and studies of cellular processes. Cook, Drug Discovery Today 1:287 (1996); Udenfriend et al., Analytical Biochemistry 161:494 (1987); Baxendale et al., Advances in Prostaglandin, Thromboxane, and Leukotriene Research (ed. Sameulsson et al.) 21:303 (New York: Raven Press, 1990); Baker et al., Analytical Biochemistry 239:20 (1996); Nelson, Analytical Biochemistry 165:287 (1987); and Cook, U.S. Pat. No. 5,665,562.

The SPAs described to date all rely on specific binding interactions, such as antibody-antigen interactions, ligand-receptor interactions, biotinylated reagents which bind to streptavidin-coated beads, chelate complex formation of the species of interest, or other interactions which rely on the precise and specific structural complementarity of binding partners. While this gives SPAs high specificity for an analyte of interest, it also requires extra steps in the preparation of reagents and the time and expense of developing a binding partner system specific to the reaction of interest. It also limits its use to those systems where specific binding partners can be found or developed. For example, specific antibodies are needed for antigen-antibody assays, specific receptors are needed for ligand-receptor assays, chelate ligands must be matched to the geometry of the ion with which they form the chelation complex, and, for a biotin-streptavidin assay, analytes must be derivatized with biotin prior to the assay. If no antibodies or receptors are available for detection of a substance, specific derivatization of the analyte with a member of a binding pair such as biotin-streptavidin is required. This can introduce additional complications in the assay. For example, if a binding member is attached to a substrate in order to follow an enzyme-catalyzed reaction, the binding member may interfere with enzyme-substrate binding, rendering the assay inaccurate or useless for determining the reaction progress.

Other SPAs have been developed based on chelation of substrates by a specific chelator. One such assay is based on the preferential binding of linear nucleotides over cyclic nucleotides to yttrium silicate in the presence of zinc sulfate. The binding is described as a complex ion chelation mechanism. (Technical notes to Amersham Life Science Phosphodiesterase [$^3$H]cAMP SPA Enzyme Assay and [$^3$H]

cGMP SPA Enzyme Assay, codes TRKQ 7090 and 7100, Amersham International Plc, Buckinghamshire, England.) Again, such an assay system requires specific matching of the chelator to the substrate, based on the spatial requirements of the chelation mechanism, and cannot be generalized.

Thus, it would be useful to develop a system providing the analytical capability of scintillation proximity assays, but eliminating the need to develop a specific binding regime for each analyte. The present invention accomplishes this goal by utilizing distinct molecular properties of an analyte of interest.

The invention provides for rapid, inexpensive and convenient quantitation of an analyte of interest, avoiding the need for separation of reactants and products and obviating the need for preparation of specific antibodies or receptors or the preparation of reagents derivatized with specific binding partners. The invention thus facilitates assays, and can be used for high-throughput screening of chemical libraries.

All references, publications and patents mentioned herein are hereby incorporated by reference herein in their entirety.

DISCLOSURE OF THE INVENTION

The present invention provides a method for analyzing a sample which contains one or more molecular species, where at least one of the molecular species can stimulate scintillation of a scintillating material essentially only when adsorbed to the surface of the scintillating material. The scintillating material has a surface capable of adsorbing at least one of the molecular species via a general molecular property-based binding interaction. The molecular species capable of stimulating scintillation and adsorbed to the surface of the scintillating material are quantitated by measuring the scintillation emitted by the scintillating material.

In a further embodiment, at least two molecular species are contained in the sample, and at least one of the molecular species has a presence, absence, or degree of general molecular property-based binding interaction with the scintillating material distinct from the remainder of the molecular species, which allows for the binding and quantitation of that particular molecular species. The general molecular property-based binding interaction can be a charge-charge interaction, a dipole-charge interaction, a dipole-dipole interaction or a hydrophobic interaction.

In a further embodiment, the aforementioned presence, absence, or degree of general molecular property-based binding interaction with the scintillating material is due to a chemical or biochemical transformation of one of the molecular species into another of the molecular species. This allows for the determination of the progress or degree of completion of the molecular transformation.

In a further embodiment, the scintillating material used is a scintillating plastic, a scintillating glass, a plastic doped with a scintillant, or a glass doped with a scintillant. The scintillating plastic can be, for instance, polystyrene doped with at least one scintillating fluor, or polyvinyltoluene doped with at least one scintillating fluor.

In yet another embodiment, when two or more molecular species are provided, one is a substrate for an enzyme-catalyzed reaction or a series of enzyme-catalyzed reactions, and at least one other is a product of the enzyme-catalyzed reaction or series of enzyme-catalyzed reactions. The product has a presence of, absence of, or degree of general molecular property-based binding affinity for the scintillating material distinct from that of the substrate, as a direct result of the enzyme-catalyzed reaction or series of enzyme-catalyzed reactions.

These enzyme catalyzed reactions can be any known in the art, including, but not limited to, kinase catalyzed reactions, lipase catalyzed reactions, phosphatase catalyzed reactions, protease catalyzed reactions, tRNA transferase catalyzed reactions, or the reaction cascade or any portion thereof for the sequential synthesis of uridinediphosphate-N-acetylmuramic acid pentapeptide catalyzed by the enzymes MurA, MurB, MurC, MurD, MurE, and MurF.

In yet a further embodiment, the method is used to evaluate the results of a high throughput screen. The method is performed on a plurality of samples, wherein the plurality of samples is used to screen individual candidate compounds for their ability to affect a molecular transformation. The candidate compounds can be potential enzyme inhibitors. In yet another embodiment, the high throughput screen is used to identify compounds which inhibit an enzyme catalyzed reaction or reactions of the reaction cascade or any portion thereof for the sequential synthesis of uridinediphosphate-N-acetylmuramic acid pentapeptide catalyzed by the enzymes MurA, MurB, MurC, MurD, MurE, and MurF; or to identify compounds which inhibit a reaction catalyzed by an enzyme such as kinase, lipase, phosphatase, protease, or tRNA transferase.

The invention also encompasses devices such as plates suitable for a direct adsorption binding assay. The plates are made of a scintillating material and can have one or more wells, or the plates can have wells coated with a scintillating material. The walls of the wells can be derivatized so as to have a positive charge, e.g. by derivatization with methyltrioctylammonium bromide; the walls of the wells can be derivatized so as to have a negative charge, e.g. by derivatization with octadecyl sulfate; or the walls of the wells can be derivatized so as to have a hydrophobic surface, e.g. by derivatization with polylysine-$N^\epsilon$-palmitate.

BEST MODE FOR CARRYING OUT THE INVENTION

Figure 1:
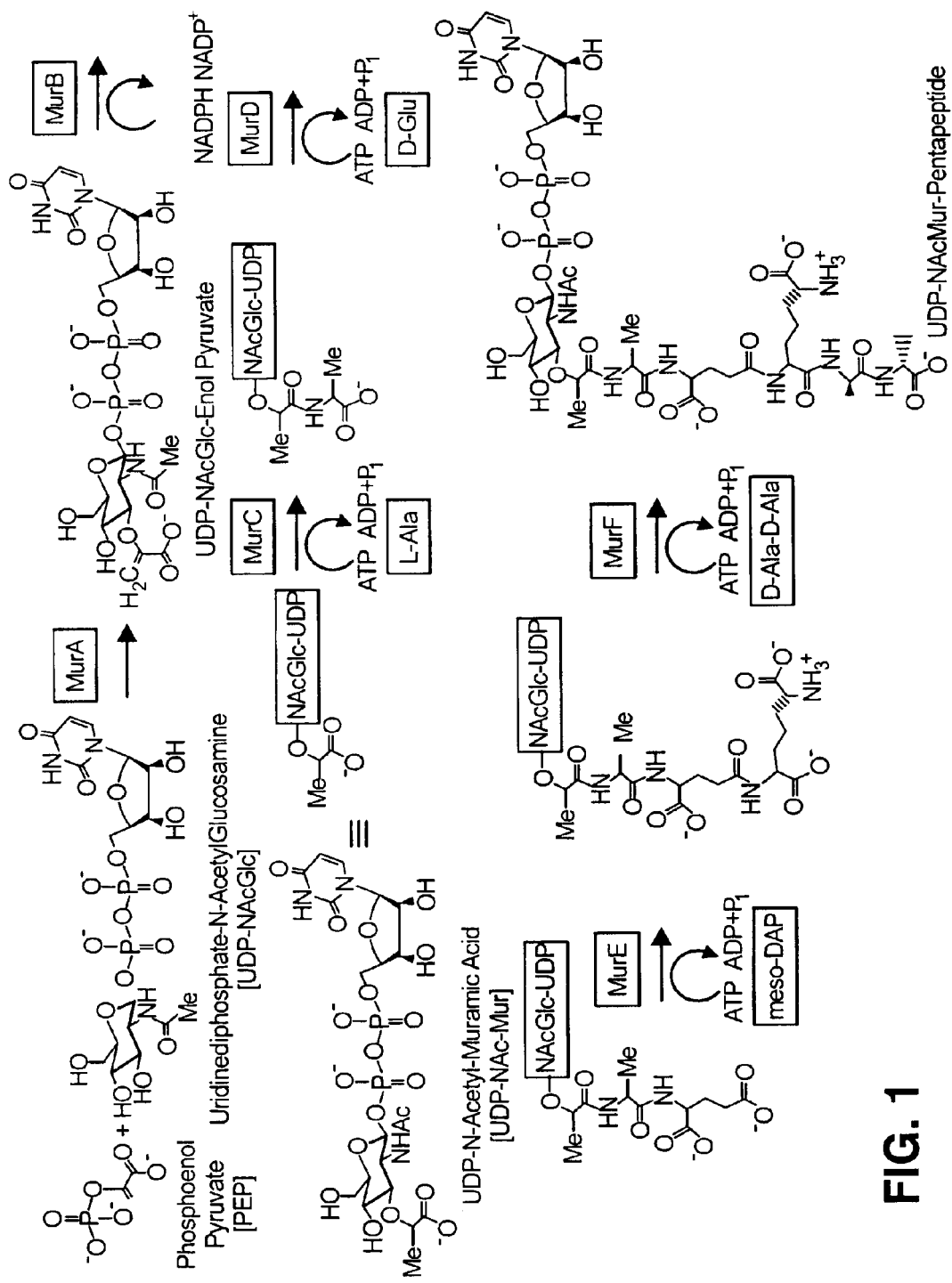
FIG. 1 depicts the reaction scheme for the sequential synthesis of Mur-pentapeptide, which can be assayed using the inventive method.

The scintillation assays described herein depend on distinct molecular properties of a radioactive analyte to accomplish the direct binding of the radioactive analyte to a scintillant, without the need for a specific binding partner for the radioactive molecule. The assays are therefore referred to as Direct Adsorption Scintillation Assays (DASAs) to distinguish them from scintillation proximity assays (SPAs), which rely on specific binding pairs. In the DASA, localization of the radioactive emitter to the scintillant is accomplished by the adsorption of the radioactive emitter, via a general molecular property-based binding interaction, directly onto the surface (or derivatized surface) of the scintillant. In contrast, in the SPA, the radioactive emitter must be bound by its specific binding partner, which in turn must be bound to the scintillant.

DASAs can be implemented using various general molecular property-based binding interactions. A "general molecular property-based binding interaction" between two substances is defined as a binding interaction which does not depend on the specific molecular geometry of both substances. Examples of general molecular property-based binding interactions include, but are not limited to, charge-charge interactions, dipole-charge interactions, dipole-dipole interactions and hydrophobic interactions.

A "specific binding interaction" is defined as an interaction which depends on the precise and specific structural complementarity of two substances involved in binding, such as embodied in antigen-antibody, ligand-receptor, biotin-streptavidin interactions. This specific complementarity is sometimes described as "lock-and-key" binding. Chelation complex formation is also defined herein as a specific binding interaction.

A "molecular species" is defined as a distinct atom or molecule. Two molecular species differ when they have different patterns of covalent connectivity; different ionization states of a molecule in solution are not considered different molecular species for the purposes of this invention. For example, alanine, the sodium salt of alanine, and the hydrochloride salt of alanine are all considered the same molecular species when in solution, while the amino acid alanine and the dipeptide alanyl-alanine are two distinct molecular species. Other examples of pairs of distinct molecular species include alanine and the methyl ester of alanine; and the α-methyl ester of glutamic acid and the γ-methyl ester of glutamic acid.

Molecular transformations are chemical reactions which result in the conversion of one molecular species into another molecular species. That is, a molecular transformation transformation alters the covalent bonding pattern of a reactant into the covalent bonding pattern of the product. The term "chemical transformation" is synonymous with the term "molecular transformation." Biochemical transformations are chemical transformations which are catalyzed by or otherwise influenced by agents, such as enzymes, derived from a biological system. For example, the hydrolysis of acetylglycine to acetic acid and glycine by boiling in 6N hydrochloric acid is a chemical transformation, while the hydrolysis of acetylglycine to acetic acid and glycine by incubation with an acylase enzyme is an example of a biochemical transformation. While all biochemical transformations are also chemical transformations, not all chemical transformations are biochemical transformations.

A "high throughput screen" is a method for evaluating a plurality of candidate compounds for a desired purpose. For example, a high throughput screen may be used to evaluate candidate compounds for enzyme inhibition. In such a screen, a plurality of samples containing enzyme, substrate, and other reagents necessary for the enzymatic reaction to proceed are provided. A different candidate compound is then added to each individual sample. The degree of completion of the enzymatic reaction (the conversion of substrate to product) is then evaluated for each sample. The samples where the enzymatic reaction did not proceed or proceeded at a slower rate (compared to the same enzymatic reaction with no added candidate compound) contain candidate compounds which act as enzyme inhibitors. High throughput screening is not limited to screening for enzyme inhibitors; high throughput screens can also be used for purposes including, but not limited to, screens for receptor agonists, receptor antagonists, and other inhibitors of specific binding reactions.

Scintillating materials suitable for use in the invention include, but are not limited to, plastic scintillants and inorganic scintillants. A scintillating material includes, but is not limited to, compounds which exhibit scintillation, and matrices such as plastic or glass which are doped with compounds that scintillate. Typical plastic scintillants include, but are not limited to, polystyrene or polyvinyltoluene matrices doped with an appropriate scintillating fluor compound. Such fluors include, but are not limited to, compounds such as para-terphenyl, quaterphenyl, p,p'-diphenylstilbene, oligophenylenes, di-t-amyl-p-terphenyl, phenyloxazol derivatives, isoquinoline derivatives, 10-hydroxybenzo[h]-quinoline, 1-phenyl-3-mesityl-2-pyrazoline, 1-p-tolyl-3-mesityl-2-pyrazoline, 1-p-tolyl-3-(2',6'-dimethoxyphenyl)-2-pyrazoline, 1-p-anisyl-3-mesityl-2-pyrazoline, 1-p-anisyl-3(2',6'-dimethoxyphenyl)-2-pyrazoline, benzoxanthene derivatives, 2,2'-bipyridine-3,3'-diol, 2-(2'-hydroxyphenyl)benzothiazole, 3-hydroxyflavone, 2,5-diphenyloxazole, 2-(4-tertiary-butylphenyl)-5-(4-biphenylyl)-1,3,4-oxadiazole, 1,4-bis-2-(5-phenyloxazolyl)-benzene, 2,5-bis-2-(5-tertiary-butylbenzoxazolyl)-thiophene, 1,4-bis-(2-methylstyryl)-benzene, anthracene, 2,5-diphenyloxazole-1,4-bis-(5-phenyloxazoly)-benzene (PPO-POPOP) or 4,4-bis-(2,5-dimethylstyryl)-benzene. One preferred plastic scintillant is p-terphenyl and p,p'-diphenylstilbene in a matrix of polyvinyltoluene (PVT) or polystyrene. Inorganic scintillants can also be used, either as the bulk material or incorporated into a plastic or glass matrix. Such inorganic scintillators include, but are not limited to, yttrium silicate doped with cerium, zinc sulphide doped with silver, and yttrium oxide doped with europium. Selection of the scintillant is determined by the characteristics of the radiation to be detected, according to principles known in the art, and other criteria including, but not limited to, ease of fabrication and cost.

The scintillating material can itself provide an appropriate surface for differential general molecular property-based molecular binding, or it can be coated or derivatized with an appropriate substance which provides such a surface. Examples of coating and derivatizing reagents which result in a positively-charged surface include, but are not limited to, tri-n-octylamine, poly-L-lysine, hexadimethine bromide (POLYBRENE), decamethonium bromide, hexamethonium bromide (all available from Sigma) and poly (diallyldimethylammonium chloride) and polyethylenimine (both available from Aldrich). With the exception of polyethylenimine, the compounds can be coated onto the wells of plates using the protocol of Example 1, below; polyethylenimine can be coated onto the wells of plates using the protocol of Example 1, but incubated at 70° C. for four hours. Examples of coating and derivatizing reagents which result in a negatively-charged surface include, but are not limited to, monoalkyl and dialkyl phosphates, and alkylsulfates and arylsulfates; a polystyrene surface may also be sulfonated by exposing the polystyrene to fuming sulfuric acid. The alkyl chains are typically $C_8$–$C_{20}$ alkyl chains; $C_8$–$C_{20}$ mono- or polyunsaturated chains can also be used. Examples of coating and derivatizing reagents which result in a hydrophobic surface include, but are not limited to, octadecylsilane and other alkylsilanes; again, the alkyl chains are typically $C_8$–$C_{20}$ alkyl chains, and $C_8$–$C_{20}$ mono- or polyunsaturated chains can also be used. In some instances, two derivatizing reagents can be used to prepare the surface of the scintillant. For example, a well coated with poly-L-lysine can be reacted with palmitic acid and a coupling reagent such as a carbodiimide to convert the positively-charged polylysine coating into a hydrophobic palmitic acid coating. Additional methods of surface derivatization are described for instance in U.S. Pat. No. 5,466,930.

Typically the scintillating material will be formed into a multiwell plate (such as a 96-well plate), or into small spheres or beads which can be suspended in solution. The scintillating material can also be used as a lining or coating for the walls of plate wells or the surface of beads when the plates or beads themselves are not made of scintillating material. In general the scintillants will be uniformly composed of a single scintillating material and, if the scintillant surface is derivatized, coated with a single derivatizing substance. However, alternative configurations can be employed. Such alternate configurations include, but are not limited to, beads where each bead is composed of two hemispheres, where each hemisphere is made of a distinct scintillating material, and wells where different regions of the well are composed of different scintillating materials. If the two materials emit scintillation at distinct wavelengths, wavelength-sensitive light detection enables discrimination of binding based on the distinct wavelengths. Another alternate configuration uses a well or bead coated in one region with one derivatizing material, and coated in another region with a different derivatizing material. The same well or bead would then be able to detect two different substances. Combinations of these configurations (different scintillating materials in different regions, coated with different derivatizing materials) can also be used.

The scintillating materials, and the coating or derivatizing materials, if present, must be stable in the solution in which the assay is conducted. The solution will typically be an aqueous solution, although in certain applications, assays will be conducted in a mixture of organic and aqueous solvents, or in completely non-aqueous solvents. Examples of such organic solvents include, but are not limited to, ethanol, methanol and other alcohols, dimethyl sulfoxide, dioxane, tetrahydrofuran, acetic acid, formic acid, and acetonitrile.

One useful embodiment of a coated scintillating material is a 96-well polystyrene microplate, with wells coated with a polystyrene-based scintillating plastic, sold under the registered trademark FLASHPLATE™ by DuPont Co. New England Nuclear Life Science Products (Boston, Mass.). For use in a DASA, the plastic scintillator can be coated with methyltrioctylammonium bromide. This provides a positively charged surface with an underlying scintillating material. When an aqueous solution containing radioactive anionic molecules contacts this coated scintillant, the anions bind via charge-charge interactions to the methyltrioctylammonium-coated surface, and induce scintillation in the underlying scintillating material. This scintillation is counted using, for instance, the TOPCOUNT™ microplate scintillation and luminescence counter (Packard Instrument Co., Meriden, Conn.).

In one embodiment, the invention can be used as an assay for enzyme-catalyzed reactions. The activities of many enzymes are difficult to measure due to the absence of change in a readily detectable signal, such as color or fluorescence intensity, over the course of the enzyme catalyzed reaction. Often, chromatographic techniques must be used for separation and detection of the distinct molecular species involved (the substrates and reaction products). This process is time consuming, and would generally preclude the use of methods such as high throughput screening for development of enzyme inhibitors.

One example of such a reaction, the sequential synthesis of uridinediphosphate-N-acetylmuramic acid pentapeptide (UDP-NAcMur-pentapeptide) from the bacterium *Escherichia coli* is depicted in FIG. 1. The six enzymes MurA, MurB, MurC, MurD, MurE, and MurF catalyze the reactions as depicted, leading to the final product. The enzyme MurA catalyzes the condensation of uridinediphosphate-N-acetylglucosamine (UDP-NAcGlc) and phosphoenol pyruvate (PEP) to produce uridinediphosphate-N-acetylglucosamine-enol pyruvate (UDP-NAcGlc-EP). MurB catalyzes the reduction of UDP-NAcGlc-EP by the reduced form of nicotinamide adenine dinucleotide phosphate (NADPH) to produce uridinediphosphate-N-acetylmuramic acid (UDP-NAc-Mur). The free carboxylate of the muramic acid moiety serves as the attachment point for N-terminal to C-terminal synthesis of the pentapeptide. As depicted in FIG. 1, MurC catalyzes the addition of L-alanine to UDP-NAc-Mur to form L-Ala-UDP-NAc-Mur. MurD catalyzes the addition of D-glutamic acid to L-Ala-UDP-NAc-Mur to form D-Glu-L-Ala-UDP-NAc-Mur. MurE catalyzes the addition of 2,6-diaminopimelic acid (DAP) to D-Glu-L-Ala-UDP-NAc-Mur to form DAP-D-Glu-L-Ala-UDP-NAc-Mur. MurF catalyzes the addition of the dipeptide D-Ala-D-Ala to DAP-D-Glu-L-Ala-UDP-NAc-Mur to form D-Ala-D-Ala-DAP-D-Glu-L-Ala-UDP-NAc-Mur (Mur-pentapeptide). Thus many different molecular species participate as reactants and products in the overall reaction scheme.

The reaction progress of each step in this cascade is difficult to follow spectroscopically due to the lack of a chromophore or fluorophore change when the various molecular species are produced or consumed. Certain current assay methods are based on phosphate release. Phosphate release is insensitive and methods employing it often cannot detect alternative substrate inhibitors, as they do not directly detect product. That is, inhibitors which can substitute for the regular enzyme substrates may also release phosphate groups during the enzyme-catalyzed reaction, but the peptidic product formed may not be able to proceed through the subsequent course of the reaction cascade and/or may exert detrimental effects on the host cell. Other current assay methods are based on isotope labeling, which involves the time-consuming separation of reaction substrate from product by chromatography. Another major difficulty in assaying these enzymes is the need to prepare the corresponding substrate for each sequential step. These substrates are not commercially available and custom preparation is time consuming and adds to the expense and complexity of the assay. For these reasons, the application of high throughput screening using these enzymes to screen for active compounds is impractical and not available currently. In contrast, the substrates used in the DASA are readily available from commercial sources, such as American radiolabeled Chemicals Inc,. of St. Louis, Mo., and Moravek Biochemicals Inc. of Brea, Calif.

The Mur-pentapeptide reaction can be followed easily by the method of the present invention. By derivatizing a 96-well scintillating plate, such as the FLASHPLATE™ (registered trademark of DuPont Co. New England Nuclear Life Science Products, Boston, Mass.) with methyltrioctylammonium bromide, a highly positively charged surface can be created on the surface of the scintillating material. The amino acid incorporated at the step of interest is tritium labeled; for example, to study the enzymatic coupling of D-Ala-D-Ala to DAP-D-Glu-L-Ala-UDP-NAc-Mur by MurF, tritiated D-Ala-D-Ala is used. The tritiated D-Ala-D-Ala is combined with the remaining substrates (UDP- NAcGlc, PEP, L-Ala, D-Glu, meso-DAP, ATP), the appropriate enzymes (MurA, MurB, MurC, MurD, MurE, and MurF), and appropriate cofactors such as NADPH. The reaction cascade is allowed to proceed for a suitable time to allow Mur-pentapeptide to accumulate. Then the reaction mixture is transferred to the 96-well scintillant plate under acidic conditions. The Mur-pentapeptide complex is highly negatively charged and will bind to the positively charged derivatized surface of the 96-well plate. As the Mur-pentapeptide incorporates the tritiated D-Ala-D-Ala, it will stimulate scintillation. However, any free D-Ala-D-Ala which was not incorporated into Mur-pentapeptide will not bind to the positively charged derivatized surface, as under acidic conditions the net charge of D-Ala-D-Ala will be zero or positive. Thus the successful completion of the six enzyme-catalyzed reactions can be monitored by the scintillation assay.

Alternatively, a different substrate can be chosen for the tritiated label, such as L-Ala; the scintillation would then reflect the overall success of the first three steps of the reaction, while subsequent steps would not affect the amount of signal measured. It should be noted that if the step catalyzed by MurD is chosen for assay, where glutamic acid is incorporated, the detection is preferably run at a low pH, e.g. about pH 2, to insure that glutamic acid is neutral or positively charged (the pKa of the gamma-carboxylate of glutamic acid is about 4.3). Those of skill in the art will recognize that certain substrates in other assays may require different conditions than the general conditions used in the assay described above, e.g. aspartic acid in a charge-based DASA. These conditions can be determined readily by one of skill in the art in light of the guidance provided herein.

In general, in order to detect changes in enzymatic activity at any step in the pathway, the enzyme/substrate concentration and reaction times are adjusted such that a decrease in activity (e.g., by inhibition) of the enzyme under investigation will result in the decrease of the scintillation signal. If one particular reaction step is of interest, one can increase the concentration of all enzymes dramatically except the concentration of the enzyme of interest, in order to make that enzyme-catalyzed reaction the rate-limiting step of the reaction. A change in activity of the enzyme of interest results in changes in scintillation signal.

One of the advantages of this system is that individual intermediates need not be prepared for each step. While previous methods for studying a single step would require, for example, prior preparation of DAP-D-Glu-L-Ala-UDP-NAc-Mur to study the MurF enzymatic step, in the presently claimed invention only the starting materials, substrates, and the appropriate tritiated amino acid need be supplied. Furthermore, no separation of reactants from products is required. No antibodies or receptors need to be prepared to specifically bind individual products or reactants. The substrates and/or products do not need to be derivatized with specific binding partners such as biotin.

Such a system is readily adaptable to use in high-throughput screening, where different test compounds can be included in a series of reaction mixtures, followed by transfer of those reaction mixtures to the multiwell scintillating plate for quantitative or qualitative analysis of the amount of scintillation stimulated. Reaction mixtures where the test compounds lead to a decrease in scintillation counts can be studied further to identify and isolate inhibitors of the enzymatic reaction step of interest.

The differential binding of two different molecular species—e.g., substrate and product—can be due either to differences in the presence or absence of one or more general molecular property-based molecular interactions, or in the degree of one or more general molecular property-based molecular interactions.

Thus, the present invention further encompasses quantitation of many other types of enzymatic reactions, including, but not limited to, reactions where at least one of the substrates is not negatively charged, but the product incorporating all or part of that substrate is negatively charged; reactions where at least one of the substrates is not positively charged, but the product incorporating all or part of that substrate is positively charged; reactions where at least one of the substrates is negatively charged, but the product incorporating all or part of that substrate is not negatively charged; reactions where at least one of the substrates is positively charged, but the product incorporating all or part of that substrate is not positively charged; reactions where at least one of the substrates is not very hydrophobic, but the product incorporating all or part of that substrate is very hydrophobic; and reactions where at least one of the substrates is very hydrophobic, but the product incorporating all or part of that substrate is not very hydrophobic.

The characteristics distinguishing substrate and product can be due to the presence or absence of a specific characteristic, i.e., the substrate is negatively charged, but the product is not; or of a different degree of a single characteristic, i.e. the substrate is only slightly hydrophobic, but the product is very hydrophobic.

One example of such a reaction is a kinase reaction which adds a phosphate group onto a peptide. Kinase peptide substrates are generally highly charged, with about 30% of the peptide residues composed of lysine or arginine. Such a peptide will bind strongly to a negatively-charged surface, such as a FLASHPLATE™ coated with a negatively-charged derivatizing agent. The peptide is incubated with the kinase and $(\gamma\text{-}^{32}P)$-ATP. The kinase will add the radioactive phosphate group of $(\gamma\text{-}^{32}P)$-ATP onto the peptide. The net charge of the peptide remains highly positive after phosphorylation. Both the phosphorylated peptide and the unphosphorylated peptide will bind to the negatively coated FLASHPLATE™ or any negatively-charged scintillant containing surface. However, only the peptide incorporating $(\gamma\text{-}^{32}P)$-phosphate will produce a scintillation signal, while the unphosphorylated peptide will not. The reaction progress can thus be followed by the increase in scintillation signal.

Another example is a lipase reaction where lipase removes a fatty acid from a water-soluble lipid. A lipid with a tritiated fatty acid chain is prepared. At acidic pH, the fatty acid will be very hydrophobic while the lipid will remain in the solution. By coating the scintillant containing surface with a suitably hydrophobic material, only the fatty acid released by the lipase will bind to the solid surface to produce a scintillation signal.

Another example is a phosphatase reaction. Phosphatase removes a phosphate group from a phosphorylated peptide. These peptides tend to have a high net positive charge at low pH, and will bind to negatively-charged surfaces, e.g. a FLASHPLATE™ coated with a negatively-charged derivatizing material. A phosphorylated peptide incorporating $^{32}P$-phosphate is used as the substrate. Once the phosphate group is removed from the parent peptide, the negatively charged phosphate will not bind to a negatively charged surface, while both the substrate peptide and product peptide will bind to such a surface. In this case, the reaction progress is monitored by following the decrease in the scintillation signal.

Another example is a protease reaction. Proteases hydrolyze peptides into at least two segments. For a reaction where two segments are formed, the two fragments are referred to here as segment A and segment B. The original peptide can be prepared so that a tritiated label is contained in the portion that will become segment B. If segment A of the peptide contains, for example, either phosphate or arginine and segment B does not, after the enzymatic reaction, the B segment alone will no longer bind to a suitably derivatized scintillation surface and reduce the scintillation signal. A suitable surface for detecting cleavage in a phosphate-containing peptide is positively charged, while a suitable surface for detecting cleavage in an arginine-containing peptide is negatively charged.

Yet another example is a tRNA transferase reaction. tRNA transferase transfers an amino acid onto a tRNA molecule during protein synthesis. A tritiated amino acid can be prepared which should not bind to the positively charged surface in an acidic solution. Once the amino acid is transferred to RNA, the amino acid-tRNA product will bind to a positively charged surface and generate a scintillation signal.

The following examples are intended to illustrate the invention, and are not intended to limit the invention in any manner.

EXAMPLES

Materials

Underivatized FLASHPLATE™s, poly-D-lysine coated FLASHPLATE™s, and L-[2, 3-$^3$H]-alanine (72.3 Ci/mmol) were obtained from NEN Life Science Products. ATP, NADPH, UDP-N-acetylglucosamine (UDP-NAcGlc), phosphoenolpyruvate (PEP), L-alanine, D-glutamate, DL-$\alpha$, $\epsilon$-diaminopimelic acid (meso-DAP), and phosphomycin were obtained from Sigma Chemicals Co. D-[2, 3$^3$H]-alanyl-D-[2, 3-$^3$H]-alanine (7 Ci/mmol) was from Moravek Biochemical Inc., Brea, Calif. Methyltrioctylammonium bromide was from Aldrich. MurA, B, C, D, E, F and UDP-MurNac were prepared by methods known in the art. The TOPCOUNT™ microplate scintillation and luminescence counter was obtained from Packard Instrument Co., Meriden, Conn. All other reagents were obtained from Sigma (Reagent Grade).

Example 1
Preparation of Derivatized Polystyrene Plates With Positive Surface Charge A 0.1% w/v solution of methyltrioctylammonium bromide (Aldrich) in water was prepared. 200 μl of the solution was added to each well of a FLASHPLATE™ and incubated at 35° C. for 2 hours. The liquid was then removed and the plates were air-dried overnight prior to use.

Example 2
Enzymatic Synthesis of L-Ala-UDP-NAc-Mur

Figure 2:
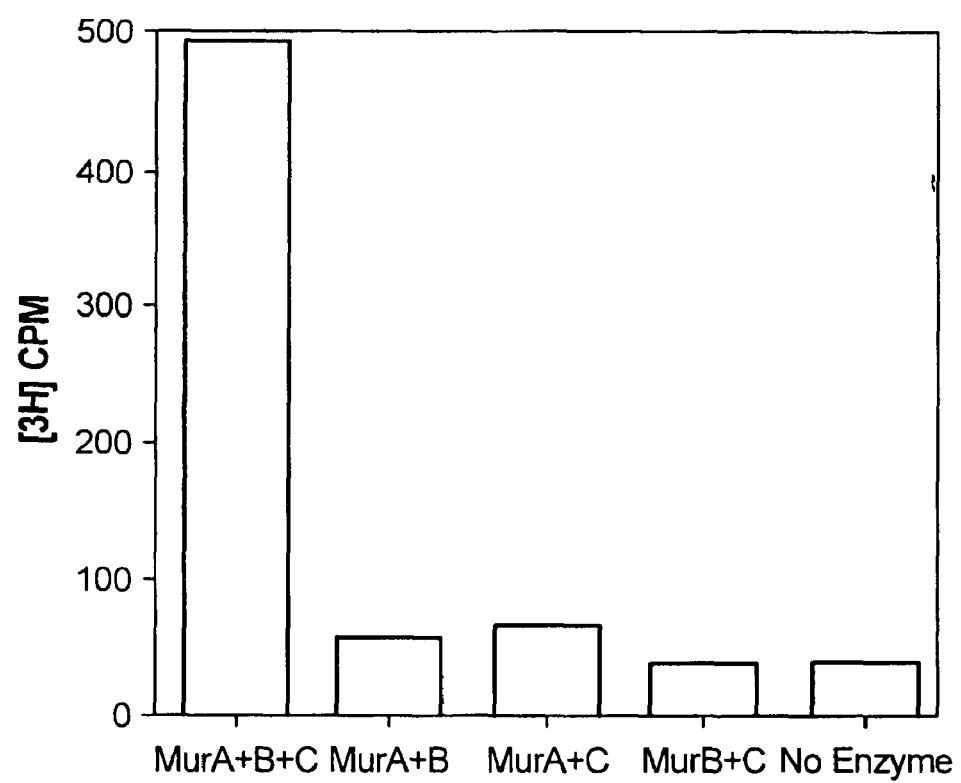
FIG. 2 is a graph illustrating the use of the assay for investigating the MurA-MurB-MurC reactions of the Mur-pentapeptide synthesis, along with negative controls.

A reaction mixture was prepared, of which 2 μl contains 38 ng MurA, 34 ng MurB, 34 ng MurC, 40 pmol ATP, 40 pmol UDP-NAcGlc, 40 pmol PEP, 40 pmol NADPH, 4 pmol L-[$^3$H]-alanine (72.3 Ci/mmol) in 50 mM Tris-HCl, pH 8, 20 mM MgCl$_2$, 20 mM (NH$_4$)$_2$SO$_4$, 1 mM DTT, 0.005% Brij-35. The mixture was incubated at room temperature for one hour. After one hour, 0.25 μl of the reaction mixture was transferred into each well of the poly-D-lysine coated FLASHPLATE™; each well contained 100 μl of 10 mM acetic acid, pH 3.0. The scintillation was counted using the TOPCOUNT™. As indicated in FIG. 2, leftmost bar labeled "MurA+B+C", when all the reaction substrates and enzymes were present, a significant signal resulted.

As negative controls, reaction mixtures were prepared missing one of the three enzymes, as well as a reaction mixture with no enzymes present. If any one of the three enzymes were missing (FIG. 2, three center bars labeled "MurA+B", "MurA+C", "MurB+C"), or if all enzymes were missing (FIG. 2, rightmost bar labeled "No enzyme"), only background signal was detected.

Example 3
Detection of Enzyme Inhibition

Figure 3:
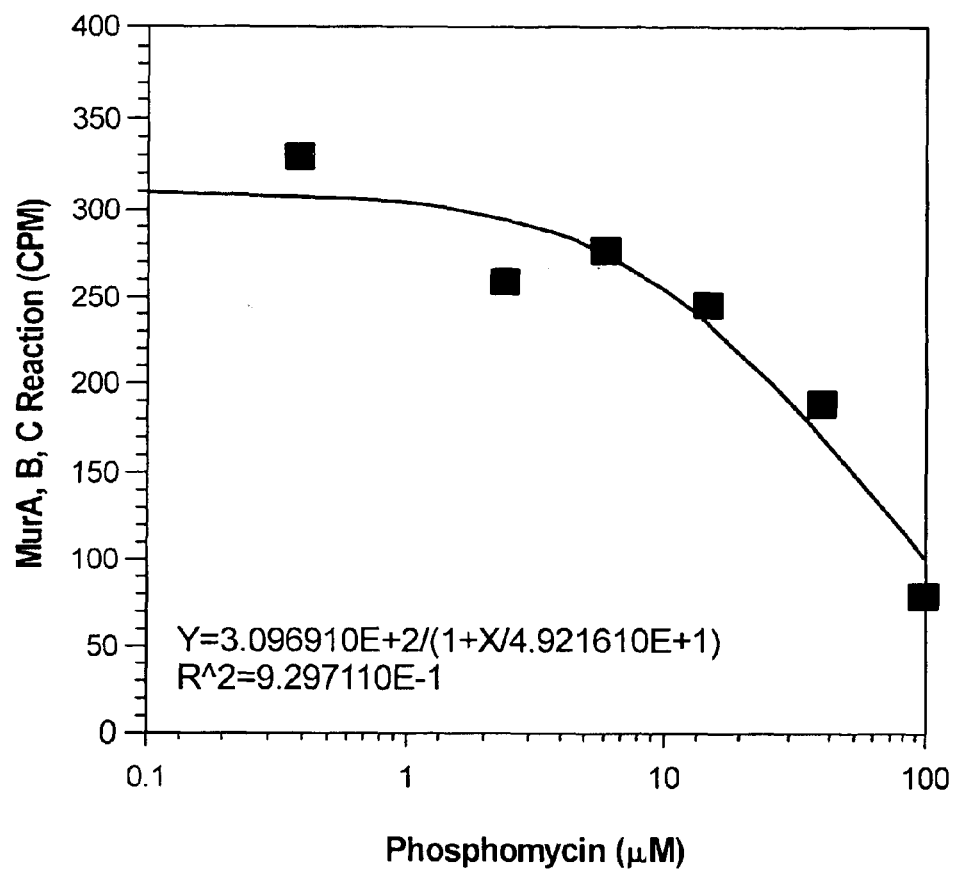
FIG. 3 is a graph which depicts the use of the assay for studying enzyme inhibition.

Enzyme mixtures (with 60 ng MurA, 8 ng MurB and 60 ng MurC present in each 2 μl sample) were prepared. Phosphomycin, a known inhibitor of MurA, was added to the reaction mixtures in different concentrations as shown in FIG. 3. The enzyme-phosphomycin mixture was pre-incubated at room temperature for 30 minutes. The substrates, as prepared in Example 2, were then added to the mixture to start the reaction. After 30 minutes of reaction at room temperature, 0.25 μl of the reaction mixture was transferred into each well of the poly-D-lysine coated FLASHPLATE™; each well contained 100 μl of 10 mM acetic acid. The scintillation was counted using the TOPCOUNT™.

The results of the experiment are shown in FIG. 3. As can be seen from the graph, increasing concentrations of inhibitor led to decreased scintillation count, demonstrating the ability of the assay to detect enzyme inhibition. The relatively high IC$_{50}$ for phosphomycin is due to the fact that the phosphomycin pre-incubation was carried out in the absence of UDP-NAc-Glu.

Example 4
Assay of MurA to MurF Enzyme Catalysis in One Reaction Mixture.

The reaction was carried out in a buffer of 50 mM Tris-HCl, pH 8.5, 0.5 mM MgCl$_2$, 0.1 mM K$_2$HPO$_4$, 2 mM DTT, and 0.005% Brij-35. 5 μl of reaction mixture contains 0.1 nmol UDP-NAcGlc, 0.1 nmol PEP, 0.4 nmol ATP, 0.1 nmol NADPH, 0.2 nmol L-alanine, 0.2 nmol D-Glu, 0.4 nmol meso-DAP, 0.1 nmol D-[H]-alanyl-D-alanine (7 Ci/mmol), 0.2 μg MurA, and 47 ng each of MurB, MurC, MurD, MurE, and MurF. The mixture was incubated at room temperature for 135 minutes. After 135 minutes, 0.5 μl of the reaction mixture was transferred into each well of the reaction plate prepared in Example 1; each well contained 200 μl of 10 mM acetic acid. The scintillation was counted using the TOPCOUNT™.

Figure 4:
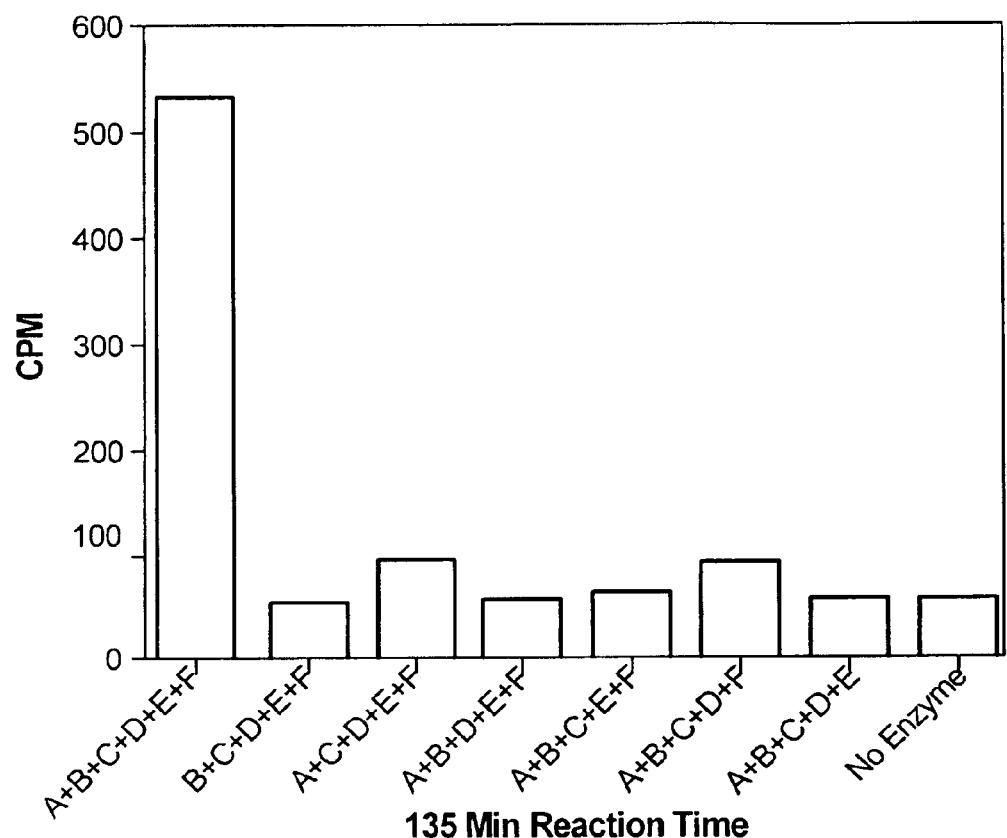
FIG. 4 is a graph illustrating the use of the assay for investigating the entire Mur-pentapeptide synthetic scheme, with negative controls.

As indicated in FIG. 4, leftmost bar, with all enzymes present, a significant amount of scintillation was detected. If any, or all, of the six enzymes were missing, only background scintillation was detected (FIGS. 4, 7 rightmost bars). It should be noted that the single reaction mixture containing all six enzymes was able to monitor the overall activity of the six different enzymes, using only commercially available substrates.

Figure 5:
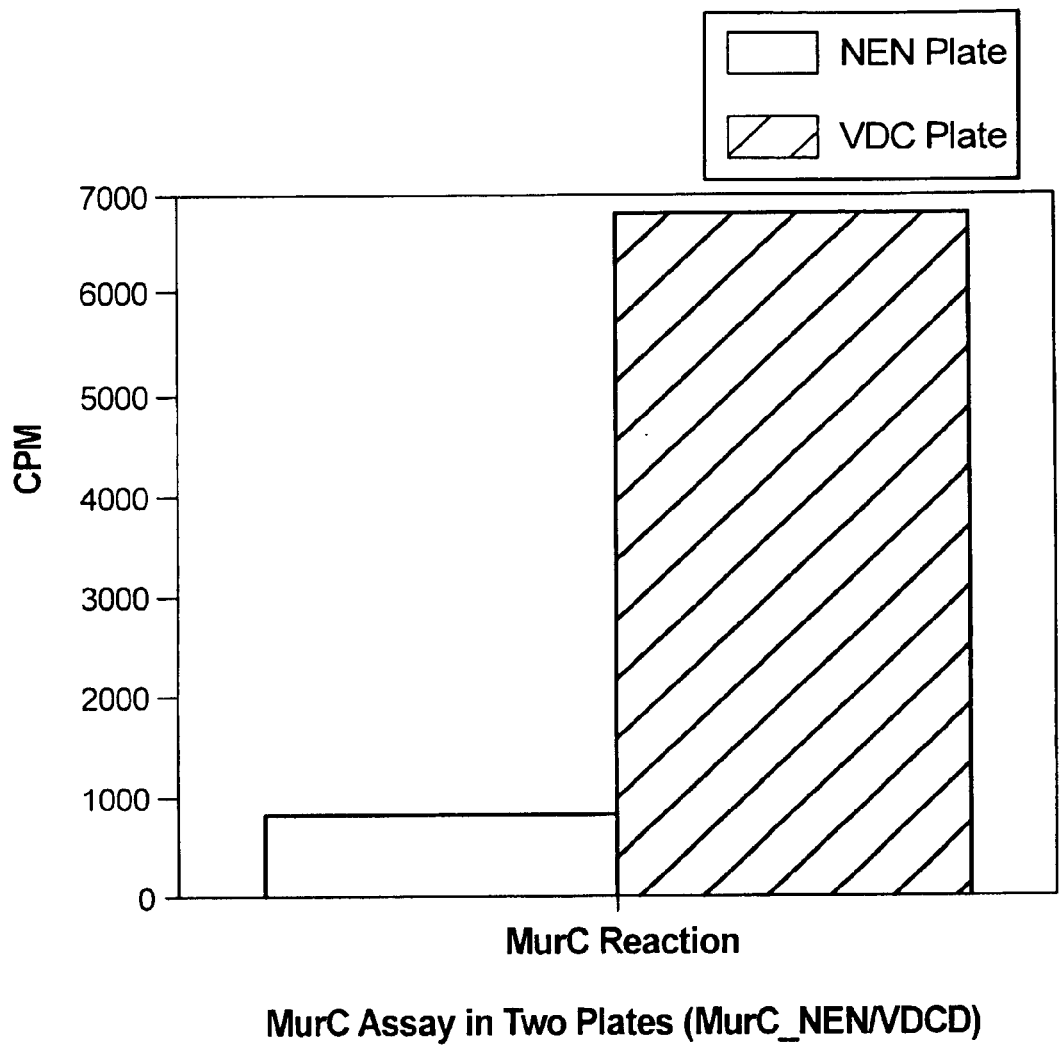
FIG. 5 is a graph comparing the performance of a plate developed to practice the inventive method to the performance of a commercially available plate.

Example 5
Comparison of Methyltrioctylammonium Bromide-treated Plate with Commercially Available Plate 0.5 μl of a reaction mixture prepared as in Example 2 was transferred into a well of the plate prepared in Example 1 containing 200 μl of 10 mM acetic acid, and into a well of the commercially available FLASHPLATE™ with wells coated with poly-D-lysine. Scintillation was quantitated using the TOPCOUNT™. The results are shown in FIG. 5, illustrating the improved sensitivity of the methyltrioctylammonium bromide derivatized plates over existing plates.

Example 6
Hydrophobic Plates: Derivatization of Plate Well Surface

200 μl of 100 μM palmitic acid and 100 μM dicyclohexylcarbodiimide in tetrahydrofuran is added to each well of a poly-L-lysine coated FLASHPLATE™ and incubated at room temperature for 2 hours. The liquid is removed and the plates are washed with several portions of tetrahydrofuran and 50% tetrahydrofuran/50% $H_2O$, then dried overnight prior to use.

Example 7
DASA Assay Utilizing Hydrophobic General Molecular Property-Based Interaction Eight samples, each comprising 20 μl of 0.25 μg/ml of human cytosolic phospholipase A2 (cPLA2) in 5 mM glycine (pH 9.0)/1 mM $CaCl_2$/225 mM NaCl/30% glycerol (v/v) with 100 uM 1-palmitoyl-2-($^3$H-arachidonyl)-phosphatidyl choline are incubated at 37° C. A sample is quenched at 0.5, 1, 2, 3, 6, 12, 18, and 24-hour time points by addition of 200 μl of Dole's reagent (isopropanol/heptane/1N $H_2SO_4$ at a 40:50:1 ratio). The organic phase of each reaction mixture is transferred to the hydrophobic plate prepared in Example 6 and the scintillation counted using the TOPCOUNT™. The $^3$H-arachidonic acid released by cPLA2 is bound by the derivatized FLASHPLATE™, while that remaining attached to phosphatidyl choline remains in solution and does not generate a scintillation signal.

Example 8
Preparation of Derivatized Polystyrene Plates With Negative Surface Charge 200 μl of a 0.2% w/v solution of octadecyl sulfate sodium salt is added to each well of a FLASHPLATE™ and incubated at 35° C. for 2 hours. The liquid is removed and the plates are air-dried overnight prior to use.

Example 9
Assay of Matrix Metalloproteinase Activity

Eight 20 μl reaction mixtures, each comprising 50 nM of the matrix metalloprotease matrilysin in 50 mM HEPES (pH 7.0)/5 mM $CaCl_2$/0.02% Brij and 50 μM of the peptide Pro-($^3$H-Leu)-Gly-Leu-Leu-Ala-Arg (SEQ I.D. NO: 1) are incubated at room temperature. Matrilysin cleaves this peptide into the two segments Pro-($^3$H-Leu)-Gly and Leu-Leu-Ala-Arg. (SEQ I.D NO: 2) At 0.5, 1, 2, 3, 6, 12, 18, and 24-hour time points, a sample is transferred to the plate prepared in Example 8; the plate wells contain 200 μl buffer solution at neutral pH. Under these conditions, both Pro-($^3$H-Leu)-Gly-Leu-Leu-Ala-Arg (SEQ ID NO: 1) and Leu-Leu-Ala-Arg (SEQ ID NO: 2) will bind to the plate, but Pro-($^3$H-Leu)-Gly will not. The reaction progress is followed by measuring the decrease in the scintillation signal using the TOPCOUNT™.

Example 10
Assay of Kinase Activity

Eight 20 μl reaction mixtures, each comprising 50 nM of protein kinase C (PKC), 10–20 μM peptide PLSRTLS-VAAKK (SEQ ID NO: 3) and 200 μM (γ-$^{32}$P)-ATP are incubated at room temperature. At 0.5, 1, 2, 3, 6, 12, 18, and 24-hour time points, a sample is transferred to the plate prepared in Example 8; the plate wells contain 200 μl buffer solution of pH>8.0. Under these conditions, all peptides will bind to the plate due to the high number of positive charges, but only those incorporating $^{32}$P will cause scintillation. The reaction progress is followed by measuring the increase in the scintillation signal using the TOPCOUNT™.

Example 11
Assay of Phosphatase Activity of Calcineurin

Eight 20 μl reaction mixtures, each comprising 40 nM of calcineurin, 2 μM phosphorylated peptide DLDVPIPGRFDRRV-S($^{32}$P-phosphate)-VAAE (SEQ I.D NO: 4) and 40 mM Tris (pH 7.5)/0.1M NaCl/6 mM $MgCl_2$/0.1 mM $CaCl_2$ are incubated at room temperature. At 0.5, 1, 2, 3, 6, 12, 18, and 24-hour time points, a sample is transferred to the plate prepared in Example 8; the plate wells contain 200 μl of 20 mM acetic acid. Under these conditions, all peptides will bind to the plate, but the $^{32}$P-phosphate released from the peptide will not. The reaction progress is followed by measuring the decrease in the scintillation signal using the TOPCOUNT™.

Although the forgoing invention has been described in some detail by way of illustration and example for purposes of clarity and understanding, it will be apparent to those skilled in the art that certain changes and modifications may be practical. Therefore, the description and examples should not be construed as limiting the scope of the invention, which is delineated by the appended claims.

---

What is claimed is:

1. A method for analyzing a sample comprising:
   a) providing a sample containing at least two molecular species, wherein at least one of the at least two molecular species provided is a substrate for an enzyme-catalyzed reaction or a series of enzyme-catalyzed reactions and another of the at least two molecular species is a product of the enzyme-catalyzed reaction or series of enzyme-catalyzed reactions, and at least one of the molecular species is capable of stimulating scintillation;
   b) providing a scintillating material, wherein the surface of the scintillating material adsorbs at least one of the molecular species via a general molecular property-based binding interaction between the molecular species and the scintillating material, and where the scintillating material is stimulated to scintillate above background by at least one of the adsorbed molecular species, but is not stimulated to scintillate above background by any molecular species which is not adsorbed;
   c) measuring the scintillation emitted by the scintillation material;
      wherein the adsorption of the molecular species to the scintillating material is due to a chemical or biochemical transformation of one of said molecular species into another of said molecular species and the substrate, prior to transformation, is not adsorbed on or into the scintillating material; and
   d) determining the progress of or degree of completion of the molecular transformation;
      wherein the reaction product of the chemical or biochemical transformation binds to the scintillating material, and at least one of the reactants of said chemical or biochemical transformation does not bind to the scintillating material.

2. The method of claim 1, wherein the general molecular property-based binding interaction is selected from the group consisting of charge-charge interactions, dipole-charge interactions, dipole-dipole interactions and hydrophobic interactions.

3. The method of claim 1, wherein the scintillating material is selected from the group consisting of scintillating plastics and scintillating glasses.

4. The method of claim 1, wherein the scintillating material is a plastic doped with a scintillant.

5. The method of claim 3, wherein the scintillating plastic is selected from the group consisting of polystyrene doped with at least one scintillating fluor and polyvinyltoluene doped with at least one scintillating fluor.

6. The method of claim 1, wherein the general molecular property-based binding affinity is due to the presence of positive charge, the absence of positive charge, the presence of negative charge, the absence of negative charge, the presence of a dipole moment, the absence of a dipole moment, the presence of hydrophobicity, or the absence of hydrophobicity.

7. The method of claim 1, wherein the enzyme catalyzed reaction is selected from the group consisting of kinase catalyzed reactions, lipase catalyzed reactions and tRNA transferase catalyzed reactions.

8. The method of claim 1, wherein the enzyme catalyzed reaction is selected from the group consisting of the reaction cascade or any portion thereof for the sequential synthesis of uridinediphosphate-N-acetylmuramic acid pentapeptide catalyzed by the enzymes MurA, MurB, MurC, MurD, MurE, and MurF.

9. The method of claim 1, wherein the enzyme catalyzed reaction is that catalyzed by MurA.

10. The method of claim 1, wherein the enzyme catalyzed reaction is that catalyzed by MurB.

11. The method of claim 1, wherein the enzyme catalyzed reaction is that catalyzed by MurC.

12. The method of claim 1, wherein the enzyme catalyzed reaction is that catalyzed by MurD.

13. The method of claim 1, wherein the enzyme catalyzed reaction is that catalyzed by MurE.

14. The method of claim 1, wherein the enzyme catalyzed reaction is that catalyzed by MurF.

15. The method of claim 1, wherein the enzyme catalyzed reaction is the reaction cascade for the sequential synthesis of uridinediphosphate-N-cetylmuramic acid pentapeptide catalyzed by the enzymes MurA, MurB, MurC, MurD, MurE, and MurF.

16. The method of claim 1, further comprising performing the method on a plurality of samples to effect a high throughput screen.

17. The method of claim 16, wherein the high throughput screen is used to identify compounds which inhibit an enzyme catalyzed reaction selected from the group consisting of the reaction cascade or any portion thereof for the sequential synthesis of uridinediphosphate-N-acetylmuramic acid pentapeptide catalyzed by the enzymes MurA, MurB, MurC, MurD, MurE, and MurF; kinase catalyzed reactions, lipase catalyzed reactions, and tRNA transferase catalyzed reactions.

* * * * *